(12) United States Patent
Soll

(10) Patent No.: US 6,745,776 B2
(45) Date of Patent: Jun. 8, 2004

(54) METHODS FOR REDUCING POSTOPERATIVE INTRAOCULAR PRESSURE

(76) Inventor: David B. Soll, 7006 Dorsam Way, Ambler, PA (US) 19002

( * ) Notice: Subject to any disclaimer, the term of this patent is extended or adjusted under 35 U.S.C. 154(b) by 0 days.

(21) Appl. No.: 09/829,464

(22) Filed: Apr. 10, 2001

(65) Prior Publication Data

US 2002/0185139 A1 Dec. 12, 2002

(51) Int. Cl.[7] ............................................... A61B 19/00
(52) U.S. Cl. ...................... 128/898; 604/521
(58) Field of Search ........................... 128/898; 604/521

(56) References Cited

U.S. PATENT DOCUMENTS

| | | | |
|---|---|---|---|
| 5,792,103 A | * 8/1998 | Schwartz et al. | ............. 604/82 |
| 6,039,943 A | 3/2000 | Karageozian et al. | |

OTHER PUBLICATIONS

American Academy of Opthalmology "Adverse Effects Associated with the Absence of Hyaluronidase in Anesthesia for Cataract Surgery" Feb. 13, 2001 www.aao.org/aao/education/library/rcr_hyaluronidase.cfm.*
Stephen R. Hein, Elimination of Sodium Hyaluronate–Induced Decrease in Outflow Facility With Hyaluronidase, *Ophthalmic Surgery*, 17, 731–734 (Nov. 1986).
I.G. Calder, Hyaluronidase and Sodium Hyaluronate in Cataract Surgery, *British Journal of Ophthalmology*, 70, 418–420 (1986).
Charita B. Rankova, Application of Hyaluronidase After Unsuccessful Trabeculectomy, *Documenta Ophthalmologica*, 80, 381–383 (1992).
Paul U. Fechner, Intraocular Use of Hyaluronidase to Dissolve Sodium Hyaluronic Acid, *Journal of Refractive Surgery*, 13, 502–503 (Sep./Oct. 1997).
Robert A. Equi, Hyaluronan Polymer Size Modulates Intraocular Pressure, *Journal of Ocular Pharmacology and Therapeutics*, 13, 289–295 (1997).

* cited by examiner

*Primary Examiner*—Corrine McDermott
*Assistant Examiner*—Thomas C. Barrett
(74) *Attorney, Agent, or Firm*—Akin Gump Strauss Hauer & Feld, L.L.P.

(57) ABSTRACT

Hyaluronic acid is commonly used as a spacer in eye surgeries such as cataract surgery, intraocular lens surgery, corneal transplant surgery and some types of glaucoma surgery. One common side effect of these surgical procedures is a postoperative rise in intraocular pressure which can be serious and can cause permanent loss of function of optic nerve fibers and, therefore, loss of visual field function as well as visual acuity function. Intraoperative and postoperative rises in intraocular pressure also occur in vitreous, retina and other posterior segment surgeries. Methods are provided for reducing the postoperative intraocular pressure in an eye to normal preoperative levels while maintaining the therapeutic effects of the hyaluronic acid. One method comprises anesthetizing the eye at the start of the surgical procedure, administering to the eye substantially concurrently amounts of hyaluronic acid and hyaluronidase and leaving the hyaluronic acid and hyaluronidase in the eye after the operative procedure.

17 Claims, No Drawings

METHODS FOR REDUCING POSTOPERATIVE INTRAOCULAR PRESSURE

BACKGROUND OF THE INVENTION

Hyaluronic acid is a natural, high molecular weight, highly viscous polymer consisting of alternating acetylglycosamine and glucuronic acid units. This acid is found in the trabecular meshwork in the vitreous humor of the eye, as well as in other locations in the body. The polymeric structure of hyaluronic acid is broken down by the enzyme hyaluronidase which cleaves the glycosidic bonds.

Hyaluronic acid, a mucopolysaccharide, has been used in eye surgery for over twenty years. High molecular weight hyaluronic acid is used primarily as a spacer during cataract and intraocular lens surgical procedures. It is also used in other ocular surgical procedures such as glaucoma, vitreous and retina surgery and in corneal transplantation. Hyaluronic acid solutions are pseudoplastic and the cellular protective qualities of hyaluronic acid are primarily related to the fact that it keeps tissue apart and therefore prevents contact trauma.

A common side effect occurring in postoperative cataract patients is a significant early, and occasionally prolonged, rise in intraocular pressure. Such a condition is sometimes serious, especially in patients with glaucomatous optic disc changes. Although the pressure increase tends to be more severe when visco-elastic agents such as hyaluronic acid are injected into the eye during surgery, the intraocular pressure can become elevated postoperatively even when such agents are not utilized. Furthermore, such a pressure increase can occur even when no additional medications are used during the surgical procedure. In some cases, it is advantageous to leave a viscoelastic agent in the eye, which often necessitates giving patients large doses of carbonic anhydrase inhibitors. These inhibitors lower the intraocular pressure by decreasing the formation of aqueous humor, a fluid that is normally secreted in the eye, by the ciliary body. Current methods for relieving postoperative pressure increases in the eye include various types of eyedrops such as beta-adrenergic blocking agents, sympathomimetic agents, miotics, alpha II selective agents, carbonic anhydrase inhibitors and prostaglandin agents. Tables listing some of these agents appeared in the *Physician's Desk Reference for Ophthalmology* 2000.

Such methods for relieving the intraocular pressure are often undesirable because of the side effects of many of these drugs. For example, carbonic anhydrase inhibitors can cause lethargy and, in some instances, disorientation. Beta-blocker medications are contraindicated in patients with breathing problems or slow heart rates. Sympathomimetic drugs can cause an increase in blood pressure. Parasympathomimetic drugs can be associated with retinal detachments in eyes with peripheral retinal and retinovascular diseases. The above medications all work to lower intraocular pressure by either decreasing aqueous humor formation or increasing the amount of aqueous humor outflow (removal) from the anterior chamber. In some instances, if significant amounts of hyaluronic acid or a similar product are left in the eye and medications are not effective in lowering the intraocular pressure, it may be necessary to surgically aspirate them. However, aspirating the remaining hyaluronic acid from a patient's anterior chamber subjects the patient to an additional operative procedure.

There remains a need in the art to improve eye surgery by reducing postoperative intraocular over-pressure without side effects, while maintaining the effectiveness of the visco-elastic agent, such as hyaluronic acid, during the course of the operation.

BRIEF SUMMARY OF THE INVENTION

According to the present invention, a method for reducing postoperative pressure in an eye comprises anesthetizing the eye, administering to the eye substantially concurrently amounts of hyaluronic acid and hyaluronidase, performing an operative procedure on the eye, and leaving all or some of the hyaluronic acid and hyaluronidase in the eye after the procedure. The hyaluronidase is administered in an amount effective to reduce the intraocular pressure to substantially pre-operative levels by breaking down the hyaluronic acid without decreasing its effectiveness during surgery nor causing side effects in the patient.

DETAILED DESCRIPTION OF THE INVENTION

According to the present invention, a method is provided for reducing the intraocular pressure buildup which often occurs following eye surgery, especially anterior segment surgery, such as cataract and corneal transplant surgery and, in some instances, glaucoma surgery. A preferred embodiment of this invention comprises anesthetizing the eye, administering to the eye substantially concurrently amounts of hyaluronic acid and hyaluronidase, performing an operative procedure on the eye, and leaving some or all of the hyaluronic acid and hyaluronidase combination in the eye after the procedure. As will be described further below, both hyaluronic acid and hyaluronidase are administered to the eye rather than administering only hyaluronic acid. In one embodiment of this invention, the hyaluronic acid and the hyaluronidase may be mixed prior to administration. It is preferred if they are mixed no longer than up to about 30 minutes prior to administration, and more preferred if they are mixed no longer than about 5 minutes to about 10 minutes prior to administration.

In a preferred embodiment, the hyaluronic acid and the hyaluronidase may be mixed substantially contemporaneously with the administration. One way to administer the two components in such a way is via a double-barreled syringe or other mixing syringe, such that mixing occurs in predetermined concentrations in the syringe or in the needle immediately prior to or during injection. Such a method eliminates the need to measure the two components, mix them, and subsequently inject the mixture.

Syringes and devices designed for the simultaneous injection of different fluids are known in the art. For example, there are syringes in which different components are loaded into separate chambers and which can be injected separately or mixed upon injection (U.S. Pat. No. 5,599,312 of Higashikawa). In some syringes of this type, the barrel is used as a mixing chamber for multiple components which are then dispensed through the needle as a mixture (U.S. Pat. No. 5,643,206 of Fischer). It is also possible to load multiple syringes, each containing a single component, into a specially designed dispenser which is configured to inject the contents of the syringes simultaneously through a needle (U.S. Pat. No. 5,876,380 of Manganini, et al.). Other useable syringes and devices will be evident to those skilled in the art.

A preferred method of administering the hyaluronic acid and hyaluronidase is by injection during anterior segment or posterior segment surgical procedures, although other methods of administration known in the art are possible as well.

It is preferred if the hyaluronic acid and the hyaluronidase are administered by injection into the anterior chamber during anterior segment ocular surgical procedures to allow the hyaluronic acid to act as a spacer during the start of the surgical procedure. In some cases of corneal transplantation, the hyaluronic acid and hyaluronidase combination may be placed on the surface of the intraocular structures prior to suturing the corneal transplant in place. This combination may also be used in posterior segment surgery, such as retina or vitreous surgery.

Hyaluronic acid is a natural, high molecular weight, viscous polymer consisting of alternating β 1–3 glucuronic and β 1–4 glucosaminidic bonds (See *The Merck Index*, monograph 4675, pages 751–752, 11$^{th}$ Ed., 1989). A preferred form of hyaluronic acid is Healon™, commercially available from Pharmacia and Upjohn Labs, Inc. Healon™ is a high molecular weight fraction of sodium hyaluronate, a polysaccharide made up of disaccharide units linked by glycosidic bonds, in a physiological buffer. The average molecular weight of sodium hyaluronate is 4 million daltons (ranging between 2 and 5 million). Healon™ GV has an average molecular weight of 5 million daltons. Although Healon™ is a preferred form, other forms of hyaluronic acid or of sodium hyaluronate may be used in this invention as well. These may include, for example, Vitrax™, commercially available from Allergen, and Amvisc™, commercially available from Bausch & Lomb, which are both preparations containing mainly hyaluronic acid. Another alternative is Viscoat™, commercially available from Alcon, which is a combination of hyaluronic acid and chondroitin sulfate.

Hyaluronidase is an enzyme which cleaves glycosidic bonds, thereby breaking down the polymeric structure of hyaluronic acid. One highly preferred form of hyaluronidase is the Wyadase™ preparation, commercially available from Wyeth-Ayerst. Alternative preparations of hyaluronidase may be used if they are highly purified. Any type of pure non-antigenic preparation of hyaluronidase can be used in this invention as well.

In this disclosure, "operative procedure" will be understood to mean any operation or surgical procedure generally performed on an eye during which intraocular pressure increases naturally or is induced, such as cataract surgery, intraocular lens surgery, corneal transplant surgery, glaucoma surgery, retinal surgery, vitreous surgery, or the like. Although this invention is described mainly in terms of cataract surgery, it is within the scope of the invention to use a similar method during other operative procedures.

The amount of hyaluronidase administered to the eye is an amount effective to reduce the intraocular pressure to a preoperative level, or slightly lower. This effective amount of hyaluronidase administered to the eye depends on the particular operative procedure. One skilled in the art will be able to determine by routine experimentation the necessary amount, based on the particular patient and procedure. In particular, the effective amount of hyaluronidase for cataract surgery and/or cataract and intraocular surgery is about 10 units per ml to about 25 units per ml, and more preferably about 15 units per ml. When used in corneal transplant surgery, about 10 units per ml to about 25 units per ml of hyaluronidase is effective, but more preferably about 15 units per ml is used. The effective amount of hyaluronidase for glaucoma surgery is about 15 units per ml to about 25 units per ml, and when used for retina or vitreous surgery, about 10 to about 25 units per ml of hyaluronidase is effective.

In some cases, the hyaluronidase alone may be administered to the eye prior to the surgical procedure by injection into the anterior chamber if the intraocular pressure is elevated. Once the intraocular pressure has been reduced to a normal level, the hyaluronidase is then preferably administered at the beginning of the procedure in combination with the hyaluronic acid. Currently, intraocular hyaluronidase is not used during anterior segment surgery to relieve the intraocular pressure. In some patients, hyaluronidase is injected into the vitreous cavity to accelerate the absorption of a vitreous hemorrhage.

Although it is preferred that only hyaluronic acid and hyaluronidase are administered to the eye to relieve the pressure, topical medications such as, but not limited to beta-blockers, alpha II agonists, prostaglandin medications, parasympathomimetic medications, and topical carbonic anhydrase drops may also be administered at the conclusion of the surgical procedure. Systemic carbonic anhydrase inhibitor medications may also be administered, such as, but not limited to acetazolamide, dichlorphenamide, ethoxzolamide and methazolamide. Additional intraocular medications can be used during the surgery as well. These may include, for example, Miochol™ (acetylcholine, commercially available from Novartis) and Miostat™ (carbachol, carbamylcholine, commercially available from Alcon). The function of these additional chemicals is to constrict the pupil and also to further enhance aqueous outflow.

Current methods of relieving postoperative intraocular pressure include aspiration of the hyaluronic acid and the use of medications such as eyedrops and/or pills. However, these methods have significant drawbacks. For example, medications have side effects and many cataract patients, as well as other eye surgical patients, are in the older age group and cannot tolerate medications well. Also, in some instances it may be necessary to aspirate much of the hyaluronic acid which may have been left in the patient's eye. In many situations it is not advisable to subject an elderly patient to this type of secondary surgical procedure.

In contrast, the method of the present invention not only has significant advantages, but also has no negative side effects on the patient or deleterious effects on the outcome of the operative procedure. As the hyaluronidase, which is added to the eye with the hyaluronic acid, relieves the intraocular pressure, it is no longer necessary to aspirate all of the hyaluronic acid from the treated eye. Eliminating the complete aspiration makes the operative procedure simpler and safer since there is less manipulation inside the eye, which could have an adverse effect on the cells within the eye. The surgery is also of shorter duration. Furthermore, as the hyaluronidase is added to the eye substantially concurrently with the hyaluronic acid, no additional procedure or medication is needed to relieve the intraocular pressure. Most important, experiments have shown that the viscoelastic properties of the hyaluronic acid during the surgical procedure are not adversely affected by the presence of hyaluronidase. The hyaluronidase works to de-polymerize the hyaluronic acid such that even if none or only some of it is aspirated, it will be broken down and not cause a pressure rise in the eye. Ideally, however, good surgical practice dictates that at least some of the hyaluronic acid-hyaluronidase combination should be aspirated if there is no surgical contraindication.

In some cases, it may be advisable to leave a visco-elastic agent such as Healon™, Viscoat™, or other space-occupying substances in the anterior chamber of the eye at the conclusion of surgery. This is especially true in positive pressure rise when the intraocular contents tend to come forward and press against the posterior surface of the cornea. If this occurs in an eye with a synthetic intraocular lens in place, pressure on the corneal endothelium can cause significant damage to the cells and subsequent corneal swelling and opacification can occur, which are associated with decreased vision. Typically, if a patient's intraocular pressure is significantly elevated at the conclusion of the operative procedure, it is necessary to give such a patient large doses of carbonic anhydrase inhibitors, as well as topical eyedrops such as beta-blockers and alpha II agonists in order to decrease aqueous formation and/or to increase aqueous outflow. These agents all have significant side effects and, in some instances, are contraindicated in patients with various types of medical conditions such as breathing problems, heart disease or high blood pressure. However, the use of hyaluronidase in these situations will eliminate the necessity of giving these patients large doses of such drugs.

Furthermore, there is a significant amount of hyaluronic acid in the trabecular meshwork. The hyaluronidase will break this down and therefore improve the outflow of the aqueous through the trabecular meshwork. The patient's intraocular pressure will therefore decrease. The combination of hyaluronidase with other anterior chamber agents, such as a methylcellulose (Ocucoat® for example, commercially available from Storz Instrument Co.), used as spacers and/or protective agents in cataract surgery, will also be efficacious in preventing significant pressure rises because it will in effect open the trabecular meshwork and allow more aqueous humor drainage by breaking down a significant amount of the hyaluronic acid present in the trabecular meshwork.

EXAMPLE 1

Effect of Hyaluronidase-Containing Mixtures on Intraocular Pressure

The effect of hyaluronidase in conjunction with hyaluronic acid on decreasing intraocular pressure is demonstrated in this example. The anterior chambers of the eyes of a series of rabbits were injected with various chemicals or combinations of chemicals in order to investigate the resulting intraocular pressure. The hyaluronidase which was utilized is sold by Wyeth-Ayerst under the trade name Wyadase™, Healon™ (hyaluronic acid) was purchased from Pharmacia and Upjohn Labs, Inc. Miochol™ and Miostat™ were purchased from Novartis and Alcon, respectively.

Sixteen healthy rabbits of the New Zealand black belted variety were divided into eight groups containing two rabbits each. The preoperative intraocular pressure of each rabbit was measured and found to be within the range of 10 to 12 mm Hg. During the experiment, the intraocular pressure of each of the rabbits was monitored for a period of 24 hours with readings taken hourly. The experiment was designed to compare the postoperative intraocular pressures resulting from the injection of Healon™ into the anterior chamber of the eye and the injection of a combination of Healon™, hyaluronidase, and/or other chemicals.

Each rabbit was anesthetized and 0.2 cc of fluid was removed from the anterior chamber of each eye using a 27 gauge needle. The fluid was then replaced with 0.2 cc of an experimental or control material. If more than one material was to be injected, the components were used in equal amounts and were mixed immediately prior to injection. The mixture was then injected into the anterior chamber of the rabbit eye. The concentration of the hyaluronidase in the mixtures was 10 units/cc.

Table 1 shows the treatment and results of the experiments performed on each of the eight pairs of rabbits. For each eye of each rabbit, the preoperative intraocular pressure, operative treatment, and highest hourly intraocular pressure (IOP) measured during the 24 hour postoperative (PO) period are shown.

| Rabbit | Eye | Preoperative Intraocular Pressure | Operative Treatment | Highest Hourly IOP Measured During 24-hr. PO Period |
|---|---|---|---|---|
| I | Right | 12 | Control- No treatment | 14 |
| I | Left | 11 | 0.2 cc aqueous removed and replaced with 0.2 cc balanced salt solution | 29 |
| II | Right | 10 | 0.2 cc aqueous removed and replaced with 0.2 cc balanced salt solution | 24 |
| II | Left | 12 | Control-No treatment | 16 |
| III | Right | 12 | 0.2 cc aqueous removed and replaced with 0.2 cc balanced salt solution | 24 |
| III | Left | 12 | 0.2 cc aqueous removed and replaced with 0.2 cc Healon | 30 |
| IV | Right | 12 | 0.2 cc aqueous removed and replaced with 0.2 cc balanced salt solution | 24 |
| IV | Left | 12 | 0.2 cc aqueous removed and replaced with 0.2 cc Healon | 30 |
| V | Right | 12 | 0.2 cc aqueous removed and replaced with 0.2 cc Healon and carbachol | 29 |
| V | Left | 10 | 0.2 cc aqueous removed and replaced with 0.2 cc Healon | 37 |
| VI | Right | 12 | 0.2 cc aqueous removed and replaced with 0.2 cc Healon | 34 |
| VI | Left | 11 | 0.2 cc aqueous removed and replaced with 0.2 cc Healon and carbachol | 27 |
| VII | Right | 12 | 0.2 cc aqueous removed and replaced with 0.2 cc Healon and Miochol | 28 |
| VII | Left | 12 | 0.2 cc aqueous removed and replaced with 0.2 cc Healon | 37 |
| VIII | Right | 10 | 0.2 cc aqueous removed and replaced with 0.2 cc Healon | 36 |
| VIII | Left | 12 | 0.2 cc aqueous removed and replaced with 0.2 cc Healon and Miochol | 25 |
| IX | Right | 11 | 0.2 cc aqueous removed and replaced with 0.2 cc Healon | 37 |
| IX | Left | 12 | 0.2 cc aqueous removed and replaced with 0.2 cc Healon and hyaluronidase | 21 |
| X | Right | 10 | 0.2 cc aqueous removed and replaced with 0.2 cc Healon | 34 |
| X | Left | 10 | 0.2 cc aqueous removed and replaced with 0.2 cc Healon and hyaluronidase | 22 |
| XI | Right | 12 | 0.2 cc aqueous removed and replaced with 0.2 cc hyaluronidase | 20 |
| XI | Left | 10 | 0.2 cc aqueous removed and replaced with 0.2 cc balanced salt solution | 21 |
| XII | Right | 11 | 0.2 cc aqueous removed and replaced with 0.2 cc hyaluronidase | 21 |
| XII | Left | 12 | 0.2 cc aqueous removed and replaced with 0.2 cc balanced salt solution | 21 |
| XIII | Right | 10 | 0.2 cc aqueous removed and replaced with 0.2 cc Healon | 34 |
| XIII | Left | 12 | 0.2 cc aqueous removed and replaced with 0.2 cc Healon, hyaluronidase and Miochol | 20 |
| XIV | Right | 11 | 0.2 cc aqueous removed and replaced with 0.2 cc Healon, hyaluronidase and Miochol | 19 |
| XIV | Left | 12 | 0.2 cc aqueous removed and replaced with 0.2 cc Healon | 34 |
| XV | Right | 10 | 0.2 cc aqueous removed and replaced with 0.2 cc Healon | 37 |
| XV | Left | 10 | 0.2 cc aqueous removed and replaced with 0.2 cc Healon, hyaluronidase and carbachol | 24 |
| XVI | Right | 11 | 0.2 cc aqueous removed and replaced with 0.2 cc Healon, hyaluronidase and carbachol | 24 |
| XVI | Left | 10 | 0.2 cc aqueous removed and replaced with 0.2 cc Healon | 36 |

It can be seen from the data that the rabbits who had a combination of Healon™ and hyaluronidase injected into their anterior chambers experienced significantly less pressure rise than those rabbits for whom Healon™ alone was injected into the anterior chambers.

EXPERIMENT 2

Effect on Postoperative Endothelium

In order to investigate the effect of hyaluronidase on the postoperative endothelium, the eyes of the rabbits from Experiment 1 were studied by performing vital staining of the corneal endothelium of the rabbits. It was determined that there was no endothelial damage when hyaluronidase was used alone, mixed with Healon™, mixed with Healon™ and carbachol or mixed with Healon™ and Miochol™. This indicates that it is safe to add hyaluronidase to the eye during surgery without any negative side effects.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for reducing postoperative intraocular pressure in an eye comprising:
   (a) anesthetizing the eye;
   (b) injecting hyaluronidase into an anterior chamber of the eye;
   (c) administering to the eye substantially concurrently amounts of hyaluronic acid and hyaluronidase;
   (d) performing an operative procedure on the eye; and
   (e) leaving the hyaluronic acid and the hyaluronidase in the eye after the procedure;
   wherein the hyaluronidase in step (c) is administered in an amount effective to reduce the intraocular pressure to substantially pre-operative levels.

2. The method according to claim 1, wherein in step (c) the hyaluronic acid and the hyaluronidase are mixed prior to administration.

3. The method according to claim 2, wherein in step (c) the hyaluronic acid and the hyaluronidase are mixed up to about 30 minutes prior to administration.

4. The method according to claim 1, wherein in step (c). the hyaluronic acid and the hyaluronidase are mixed substantially contemporaneously with the administration.

5. The method according to claim 1, wherein in step (c) the hyaluronic acid and hyaluronidase are administered by injection.

6. The method according to claim 5, wherein in step (c) the hyaluronic acid and the hyaluronidase are injected simultaneously using a double barreled syringe or mixing syringe.

7. The method according to claim 5, wherein in step (c) the hyaluronic acid and the hyaluronidase are injected into an anterior chamber of the eye.

8. The method according to claim 1, wherein the operative procedure is selected from the group consisting of cataract surgery, glaucoma surgery, intraocular lens surgery, corneal transplant surgery, retina surgery and vitreous surgery.

9. The method according to claim 8, wherein the operative procedure is cataract surgery and the effective amount of the hyaluronidase administered to the eye is about 10 to about 25 units per ml.

10. The method according to claim 8, wherein the operative procedure is glaucoma surgery and the effective amount of hyaluronidase administered to the eye is about 15 to about 25 units per ml.

11. The method according to claim 8, wherein the operative procedure is intraocular lens surgery and the effective amount of hyaluronidase administered to the eye is about 10 to about 20 units per ml.

12. The method according to claim 8, wherein the operative procedure is corneal transplant surgery and the effective amount of hyaluronidase administered to the eye is about 10 to about 25 units per ml.

13. The method according to claim 8, wherein the operative procedure is retina or vitreous surgery and the effective amount of hyaluronidase administered to the eye is about 10 to about 25 units per ml.

14. The method according to claim 1, wherein in step (c) the hyaluronic acid and the hyaluronidase are administered to the eye prior to or during the operative procedure.

15. The method according to claim 1, wherein step (b) further comprises administering an additional medication to the eye.

16. The method according to claim 15, wherein the additional medication is a topical medication selected from the group consisting of beta-blocker medications, alpha II agonists, prostaglandin medications, parasympathomimetic medications and topical anhydrase drops.

17. The method according to claim 15, wherein the additional medication is a systemic carbonic anhydrase inhibitor selected from the group consisting of acetazolamide, dichlorphenamide, ethoxzolamide and methazolamide.

* * * * *